(12) United States Patent
Henry et al.

(10) Patent No.: US 6,936,834 B2
(45) Date of Patent: Aug. 30, 2005

(54) METHOD AND APPARATUS FOR DETERMINING STONE CELLS IN PAPER OR PULP

(75) Inventors: Deborah Jean Henry, Sherwood Park (CA); Ross S. Chow, Sherwood Park (CA); Hongqi Yuan, Edmonton (CA)

(73) Assignee: Alberta Research Council Inc., Edmonton (CA)

( * ) Notice: Subject to any disclaimer, the term of this patent is extended or adjusted under 35 U.S.C. 154(b) by 369 days.

(21) Appl. No.: 10/205,443

(22) Filed: Jul. 26, 2002

(65) Prior Publication Data

US 2003/0020029 A1 Jan. 30, 2003

(30) Foreign Application Priority Data

Jul. 26, 2001 (CA) ............................................. 2354202

(51) Int. Cl.[7] .............................................. G01N 21/86
(52) U.S. Cl. ....................... 250/559.4; 250/556; 356/71
(58) Field of Search ......................... 250/559.4, 559.45, 250/556, 559.42, 222.1, 484.2; 356/71, 430, 238.1, 238.2, 238.3

(56) References Cited

U.S. PATENT DOCUMENTS

| | | |
|---|---|---|
| 4,275,299 A | 6/1981 | Favre |
| 4,837,446 A | 6/1989 | Renard et al. |
| 5,216,483 A | 6/1993 | Berthold et al. |
| 6,061,128 A * | 5/2000 | Zweig et al. ............. 356/243.4 |
| 6,369,882 B1 | 4/2002 | Bruner et al. |
| 6,570,653 B2 | 5/2003 | Bruner et al. |
| 2002/0117274 A1 | 8/2002 | Jang |

FOREIGN PATENT DOCUMENTS

| | | |
|---|---|---|
| CA | 2078183 | 5/1993 |
| CA | 2392294 | 6/2002 |
| WO | WO 00/67002 | 11/2000 |

OTHER PUBLICATIONS

H.J. Haakanen et al., "Laser–Induced Fluorescence Imaging of Paper Surfaces," Applied Spectroscopy, 47(12), 1993, 2122–2125, month unknown.
J. A. Olmstead et al. "Fluorescence Spectroscopy of Cellulose, Lignin and Mechanical Pulps: A Review," Journal of Pulp and Paper Science, 23(12) 1997, 571–581, month unknown.
www.econotech.com/newsletters/007_fall_99.pdf.
http://www.jlfiberservices.com/optima_online/pdf/vol7_no3.pdf, no date.

* cited by examiner

Primary Examiner—Que T. Lee
(74) Attorney, Agent, or Firm—Freedman & Associates (57) ABSTRACT

Disclosed is a method and apparatus for determining stone cells within a sample of wood pulp or paper. According to the instant invention a portion of the sample is irradiated with light at a predetermined wavelength or within a predetermined range of wavelengths. The incident light causes those areas of the sample that are occupied by stone cells to fluoresce strongly relative to the background matrix of wood pulp or paper. The strongly fluorescing stone cells are registered digitally using a detector, or are observed visually by an operator viewing the sample through an ocular device. The absolute number of stone cells per unit area or a stone cell size-distribution-plot is obtained using one of automated or manual image analysis.

34 Claims, 8 Drawing Sheets

METHOD AND APPARATUS FOR DETERMINING STONE CELLS IN PAPER OR PULP

FIELD OF THE INVENTION

The instant invention relates to a method and apparatus for determining sclereids (stone cells) in paper or pulp and more particularly to a method and apparatus using fluorescence to characterize stone cells in paper or pulp.

BACKGROUND OF THE INVENTION

A sclereid is a type of thick walled highly lignified cell found in many plants. Sclereids that are found in trees are called stone cells. Stone cells can be found in the cortex, phloem and pith of several species of either hardwood or softwood trees. They are most commonly found in the bark of the tree. When pulp and paper mills use tree species that contain stone cells and use the whole tree with no debarking, when debarking is not efficient (as in the winter), or when species are used which contain stone cells in the heart of the tree, the stone cells will appear in the finished product. This is true for both chemical and mechanical pulps. Furthermore, some stone cells remain in the final product even after additional measures are taken to remove them.

Stone cells that are present in the papermakers furnish often cause difficulties. For instance, in papermaking mills where high-speed paper machines are employed the stone cells may produce areas of weakness on the forming sheet, resulting in more frequent breakage thereof. Breaks on the paper result in down time and loss of production. Accordingly, the number of stone cells is a quality issue in pulp, and pulp is commonly sold with a maximum stone cell count specification.

Furthermore, stone cells cause problems for the end user. A stone cell on a calendared sheet of paper causes an opaque spot, often referred to as a fish eye, to form. Fish eyes are undesirable, as they shed ink and show up as flaws in the print.

Currently there is no universal method for determining and quantifying stone cells. The methods currently in use are time consuming and operator dependent. Furthermore, many mills have adopted their own, in house methods for determining stone cells.

One method relies upon the hardness of the stone cell as a way of identifying a stone cell within a fiber matrix. In a dark room a light source is placed at an angle to a non-calendared hand sheet that is made using either standard method TAPPI T 205 or CPPA C.4. Where a shadow appears, the bump causing the shadow is checked to see if the bump is solid, for instance by rubbing the bump with a pencil. A hard bump is counted as a stone cell. This method is very time consuming and is highly operator dependant.

Another method relies upon the tendency of stone cells to form fish eyes. The method involves making a standard hand sheet as described above, and then calendaring the sheet between two hardened steel rollers under several hundred pounds of hydraulic pressure. The hand sheet is then put onto a light box and the places where the paper has circular opaque spots are counted as stone cells. Unfortunately, the fish eyes can be very small and poor hand sheet preparation renders them difficult to see. This method also is highly operator dependant.

In yet another method, a sample of a bleached kraft pulp stock is stained, spread in a thin layer, and examined in transmitted light. Differences in color, size and opacity make the stone cells easer to identify. Unfortunately, both the pulp stock and the stone cells take up the stain, and as such the differences in colour and opacity may not be easily discernable using transmitted light. Further, a same stain may be useful for one pulp stock and less useful for another rendering the application of the method more complex than desired.

An instrument for determining stone cells has been developed by Optest Equipment Inc., which uses a hand sheet of a known weight, thickness, and diameter that is put over a source of light. The instrument includes a camera mounted above the sample to look for subtle colour differences in a magnified, and therefore small, portion of the hand sheet. Areas of the hand sheet having a colour different from that of the surrounding fiber matrix are counted as stone cells. Of course, the small sample size is a major drawback of this method. Furthermore, stone cells often are of a similar colour compared to the surrounding fiber matrix, making such a colour based determination of stone cells difficult and unreliable. It is a further disadvantage that the instrument must be calibrated prior to analysis and that all parameters must remain constant from sample to sample in order for the instrument to stay in calibration.

Thus, it has been a continuing problem to provide a method and apparatus for quantifying stone cell content of paper or pulp. In addition, there has been a long-standing, unfulfilled need for a universal method for quantifying stone cell content of paper or pulp that is at a same time rapid and substantially operator independent.

SUMMARY OF THE INVENTION

A method according to the instant invention includes the steps of: irradiating a portion of the sample with light in a predetermined wavelength range, the predetermined wavelength range selected to induce some of the portion of the sample to emit light in a second other wavelength range by fluorescence; detecting with a detector an intensity of the light in the second other wavelength range emitted from some of the portion of the sample; and, registering a stone cell within the portion of the sample in dependence upon the detected intensity being within a predetermined range of intensity values.

Another method according to the instant invention includes the steps of: providing a sample of wood pulp or paper; irradiating a portion of the sample with light in a predetermined wavelength range, the predetermined wavelength range selected to induce some of the portion of the sample to emit light in a second other wavelength range by fluorescence; detecting with a detector an intensity of the light emitted in the second other wavelength range from some of the portion of the sample; and determining the quality factor for the portion of the sample in dependence upon the detected intensity and a known threshold value.

Yet another method according to the instant invention includes the steps of: providing a light source for irradiating a first portion of the sample with light in a predetermined wavelength range, the predetermined wavelength range selected to induce some of the first portion of the sample to emit light in a second other wavelength range by fluorescence; detecting an intensity of the light emitted in the second other wavelength range from some of the first portion; moving the sample relative to the light source to irradiate a second other portion of the sample with light in the predetermined wavelength range; detecting an intensity of the light emitted in the second other wavelength range from some of the second portion; and, when the detected intensity of the light emitted from some of the second portion exceeds the detected intensity of the light emitted from some of the first portion by a predetermined threshold value, registering an occurrence of a stone cell within the second portion.

An apparatus according to the instant invention includes: a holder (3) for holding a sample of wood pulp or paper having therein stone cells; a light source (1) for irradiating a portion of the sample with light including light within a predetermined wavelength range, for inducing the portion of the sample to emit light in a second other wavelength range by fluorescence; a detector (4) for detecting an intensity of the light emitted in the second other wavelength range from the portion of the sample and for providing a signal in dependence thereof; and, an analyzer (6) for analyzing the signal provided by the detector to determine a quality factor for the portion of the sample in dependence upon the detected intensity.

BRIEF DESCRIPTION OF THE DRAWINGS

Exemplary embodiments of the invention will now be described in conjunction with the following drawings, in which.

DETAILED DESCRIPTION OF INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein. For instance, the method and apparatus have been described in terms of a particular example in which a determination of stone cells within a paper or pulp sample is made. Of course, the determination of stone cells is but one example of a plurality of quality factors relating to a paper or pulp sample. Other examples of quality factors that may be determined using the method and apparatus according to the instant invention include amount of residual lignin within a paper or pulp sample, brightness of a paper or pulp sample, etc.

The instant invention provides a method and apparatus for determining stone cells in paper or pulp that is based upon fluorescence measurements. In particular, stone cells are highly lignified, and it is the high concentration of lignin in the stone cells that is believed to be responsible for the emission of light within the second other wavelength range.

The instant invention is described generally in terms of stone cell determination, which is a property that is linked to pulp and paper quality. For instance, lignin is highly concentrated within stone cells, which produces the intense emission of light that is used to identify the stone cells according to the instant invention. Of course, one skilled in the art will recognize that the instant invention is also useful for determining other properties relating to the quality of pulp and paper. For instance, lignin is present at a lower concentration within the fiber matrix that surrounds the stone cells. In fact, the partial removal of this lignin within the fiber matrix is the object of a delignification step in the pulp and paper making process. It would therefore be desirable to provide a method and apparatus for measuring the amount of residual lignin that remains in a pulp or paper sample after delignification.

The instant invention embodies such a method and apparatus for measuring the amount of residual lignin, or a property relating to the amount of residual lignin, in a pulp or paper sample. For instance, such a method includes the steps of: calibrating a fluorescence detector using at least one of a standard sample, a sample blank, an absolute scale etc.; irradiating a region of a pulp or paper sample containing a fiber matrix using light in a predetermined wavelength range; detecting an intensity of light emitted in a second other wavelength range; analyzing the intensity of emitted light; and, comparing the intensity of emitted light to a known calibration value to determine an amount of residual lignin in the pulp or paper sample. Optionally, the intensity of emitted light is related to one of a weight percentage of residual lignin, delignification efficiency, brightness of the sample, etc. An apparatus for use with this method includes an on-line apparatus for automatically sampling and determining the property relating to the amount of residual lignin. Optionally, the on-line apparatus includes a feedback circuit for controlling an input component of the process, such as a delignification agent, to achieve a desired result in dependence upon the measurement. Further optionally, an apparatus such as the one described below is used by an operator to measure the property relating to the amount of residual lignin in an automated or semi-automated fashion.

Advantageously, hand sheets containing wet or dry samples of pulp may be analyzed to determine if a desired delignification has been achieved during processing of wood pulp.

Of course, when testing for stone cells it is necessary to look for a few stone cells being carried within a much larger sample matrix of either paper or pulp. The prior art methods, in which portions of the sample under investigation are inspected manually for the occurrence of stone cells, are not well suited for the analysis of samples having large a surface area. Advantageously, the method and apparatus according to the instant invention accommodates larger sample sizes that will give better, and more statistically meaningful, data.

For instance, using automated image analysis to analyze a plurality of separate images from different portions of the sample allows a stone cell size-distribution-plot to be obtained. Further advantageously, information about the relative number of stone cells of different sizes is available, which is useful when determining the overall quality of the wood pulp or paper. Still further advantageously, fluorescence techniques produce extreme contrast, making the determination of what is and what is not a stone cell easier.

The determination of a stone cell within the pulp matrix is made possible by the fact the stone cell fluoresces strongly while the surrounding pulp does not. High contrast images are obtained under these conditions in which the stone cells appear as bright spots whose dimension and number are quantified using one of automated and manual means for quantification. The instant invention is useful for determining stone cells within the finished product, such as to determine the quality of paper produced from a particular batch of pulp. Advantageously, the instant invention is also useful for determining stone cells within pulp samples spread out on a non-reflecting background, such as to determine the efficiency of centrifugal cleaners in the pulp processing plant.

Figure 1:
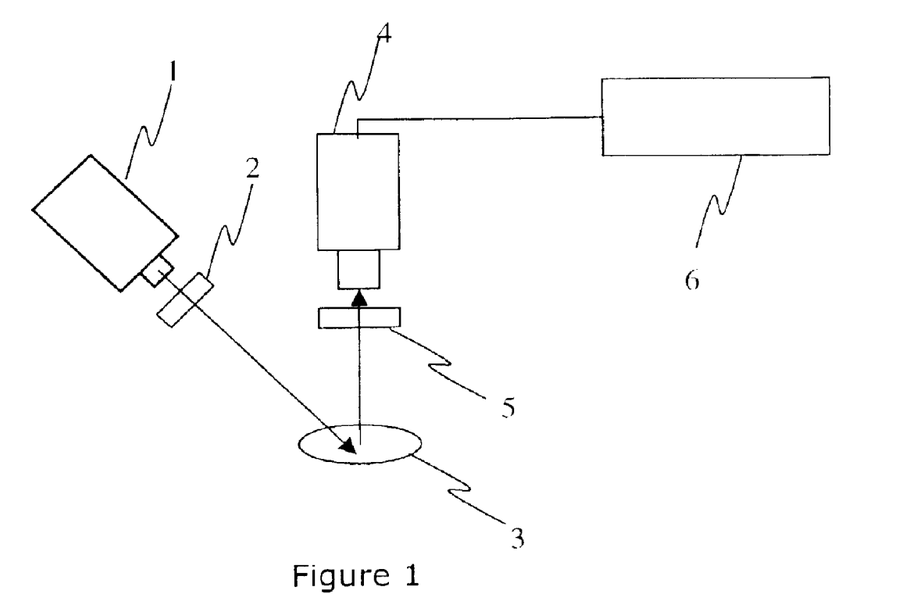
FIG. 1 is a schematic block diagram of an apparatus according to the instant invention.

Referring to FIG. 1, shown is an apparatus according to the instant invention. The apparatus includes a light source 1 for irradiating a portion of a sample mounted on a sample holder 3, with light within a predetermined range of wavelengths or at a predetermined wavelength. For example, the light source 1 is selected from a group comprising: a mercury vapor lamp; a deuterium lamp; a tungsten filament lamp; and, a laser. Optionally, more than one light source is provided in order to cover a wider wavelength range. A filter 2 is provided to filter the incident light, for instance the filter 2 excludes any incident wavelengths above 550 nm. A second other filter 5 is disposed between the sample holder 3 and the detector 4 to prevent incident light from reaching the detector 4. Filtering the incident light enhances the contrast between the stone cells and the surrounding pulp or paper matrix. Optionally, the filter 2 is omitted when the light source 1 is provided in the form of a laser. The detector 4 includes means for producing an image of the portion of the sample 3. For instance, the detector 4 is a charge coupled device (CCD) camera for providing a digitized image comprising a plurality of individual pixels, each pixel variable across a grayscale having, for example, 256 possible discrete values. Of course, optionally other than 256 possible discrete values are supported. Furthermore, detectors other than a CCD camera are suitable for use with the instant invention, including detectors which allow the second filter 5 to be omitted.

The image thus obtained by the detector 4 is provided to an image analyzer 6. The image analyzer comprises a processor (not shown) for executing program code stored within a computer readable medium (not shown) to automatically analyze the image and to determine areas of strong fluorescence, for instance areas of the sample represented by individual pixels having a value of approximately 256. Of course, the actual value that is used to define a bright spot may be less than 256 and may include a range of allowable values.

Optionally, the sample is mounted on an x-y table (not shown) for moving the sample in a controlled manner such that different portions of the sample can be irradiated, for instance in a raster fashion. Further optionally, the x-y table is under the control of a processor such that the sample is scanned automatically according to a predetermined pattern. This allows other detectors, such as for example a photodiode detector, to be used to scan the sample for the occurrence of stone cells. Still further optionally, the apparatus of FIG. 1 includes a feedback control circuit (not shown) for controlling an input component of the process, such as a delignification agent, to achieve a desired result in dependence upon the measurement.

Figure 2:
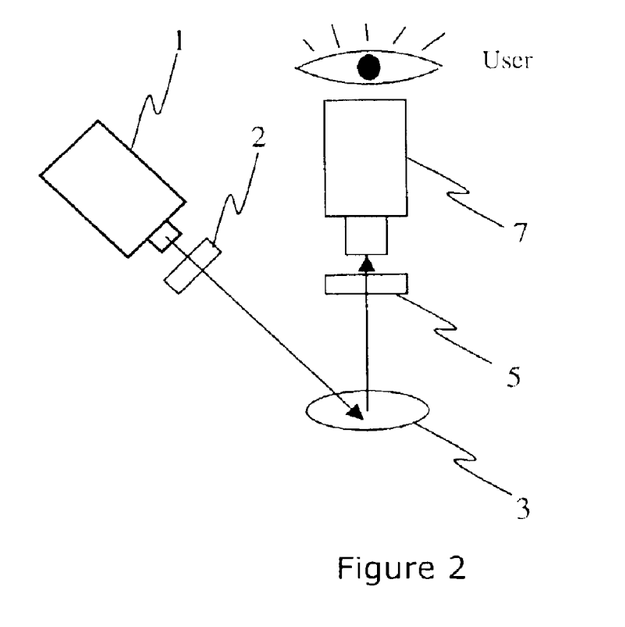
FIG. 2 is a schematic block diagram of another apparatus according to the instant invention.

Referring now to FIG. 2, shown is another apparatus according to the instant invention. Drawing elements identical to those described with reference to FIG. 1 and having identical function have been assigned like numbers. In the apparatus shown in FIG. 2, the detector 4 is replaced by one of a lens and a system of lenses 7. A user observes the filtered light directly, and quantification of the stone cells in the sample is performed manually, for instance by counting an absolute number of stone cells per unit area. Of course, the user performs the function of the image analyzer 6, which was described with reference to FIG. 1. Optionally, the sample is mounted on an x-y table (not shown) for moving the sample in a controlled manner such that different portions of the sample can be irradiated, for instance in a raster fashion.

Figure 3:
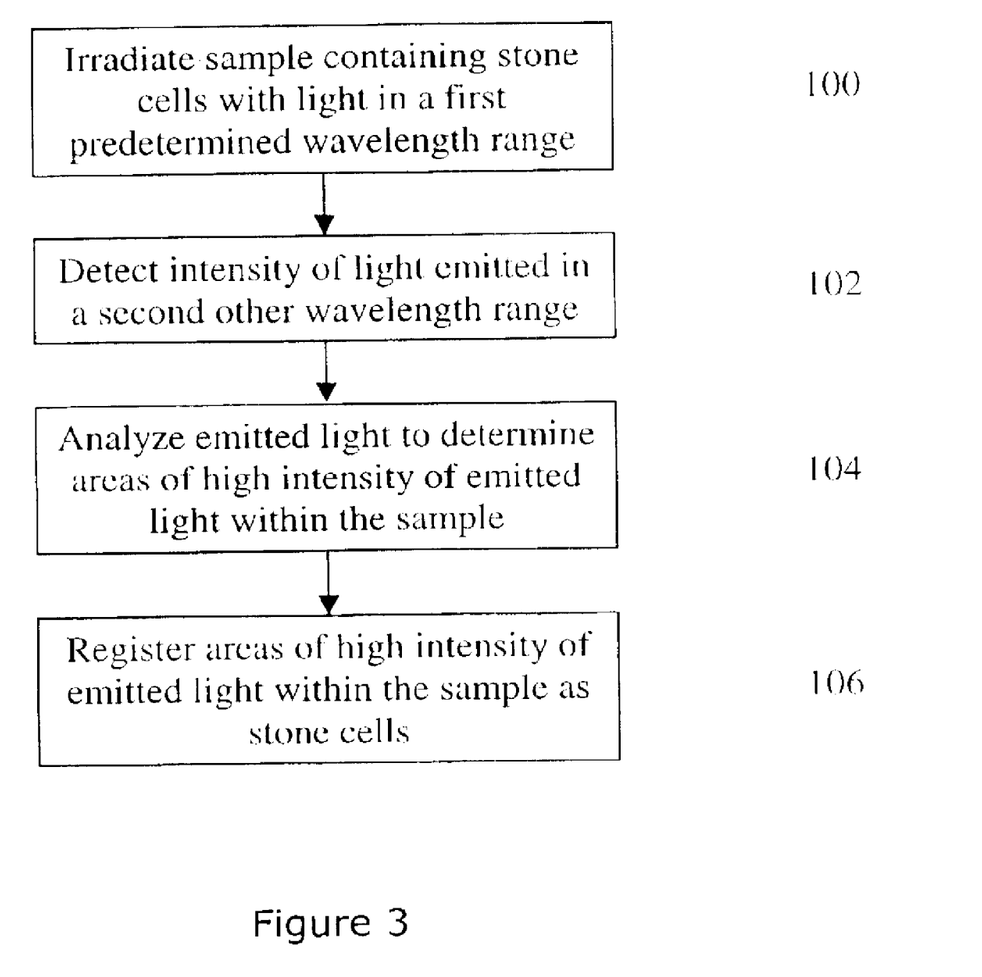
FIG. 3 is a simplified flow diagram of a method according to the instant invention.

Referring now to FIG. 3, shown is a method according to the instant invention. At step 100 a sample containing stone cells is irradiated with light in a first predetermined wavelength range. The predetermined wavelength range is selected to induce the portion of the sample to emit light in a second other wavelength range by fluorescence. At step 102, an intensity of the light emitted in the second other wavelength range is detected. The emitted light is analyzed at step 104 to determine areas of high intensity of emitted light within the sample. Areas of high intensity of emitted light are registered as stone cells within the sample at step 106.

Optionally, a radiation source that emits light in other than the 200 to 550 nm wavelength range is used. Further optionally, an image of the portion of the sample that is being irradiated is captured. Preferably the image is captured absent magnification. More preferably, the image is a digital image comprising a plurality of individual pixels, each pixel variable across a grayscale having, for example, 256 possible discrete values. Still further optionally, the step of detecting the intensity of the light is performed by a user observing through an ocular device light areas and dark areas within the portion of the sample being irradiated by light at the predetermined wavelength.

Figure 4:
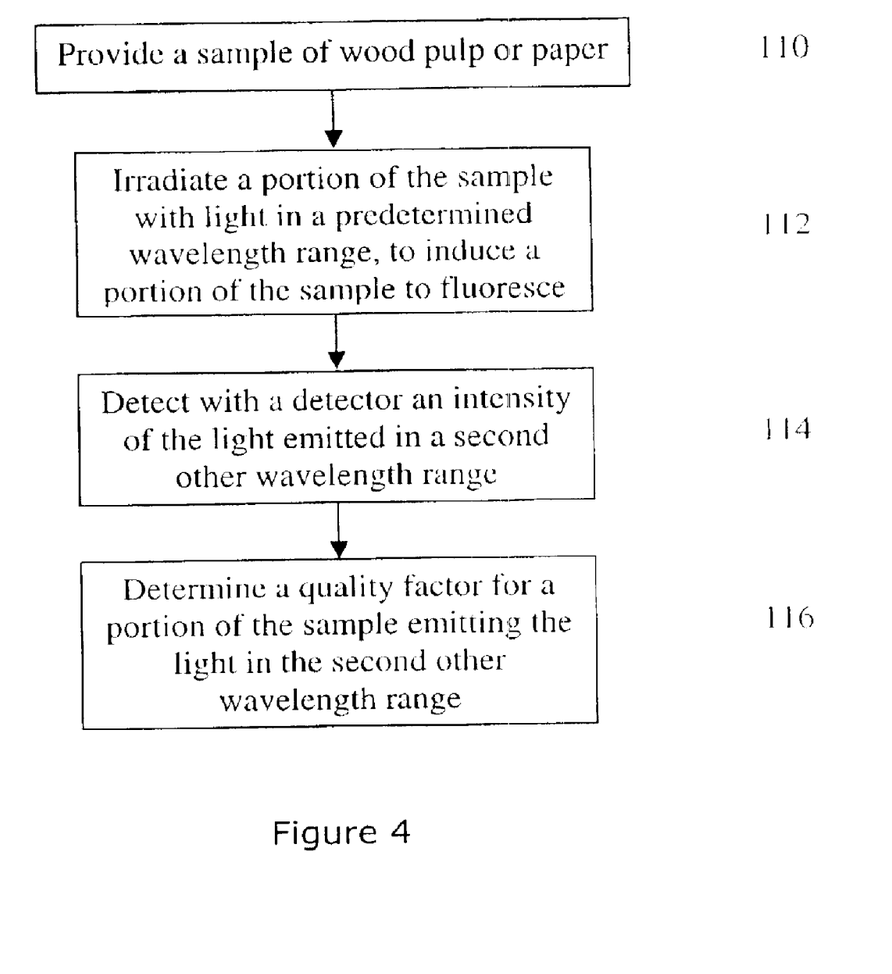
FIG. 4 is a simplified flow diagram of another method according to the instant invention.

Referring now to FIG. 4, shown is another method according to the instant invention. At step 110 a sample of wood pulp or paper is provided. A portion of the sample is irradiated with light in a predetermined wavelength range at step 112, to induce some of the portion of the sample to emit light in a second other wavelength range by fluorescence. At step 114, an intensity of the emitted light in the second other wavelength range is detected using a detector. At step 116 a quality factor is determined for the portion of the sample emitting the light in the second other wavelength range, in dependence upon the detected intensity and a known threshold value. By way of specific and non-limiting examples, the quality factor is one of an indication of a stone cell within the portion, an indication relating to a size of a stone cell within the portion, an indication of an absence of stone cells within the portion, a factor relating to an amount of residual lignin within the portion, a factor relating to a brightness of the sample within the portion, a factor relating to a whiteness of the sample within the portion, and a factor relating to a delignification efficiency for the sample. When, for instance, the quality factor is indicative of a location of a stone cell within the portion of the sample, then the known threshold value is a value that is indicative of an emission of light in the second other wavelength range that is strong relative to an emission of light in the second other wavelength range from a non-stone cell portion of the sample. Optionally, the known threshold value is determined by a step of calibration. Further optionally, the step of calibration includes the step of adjusting a sensitivity of the detector such that an output value from the detector is indicative of the quality factor.

Figure 5:
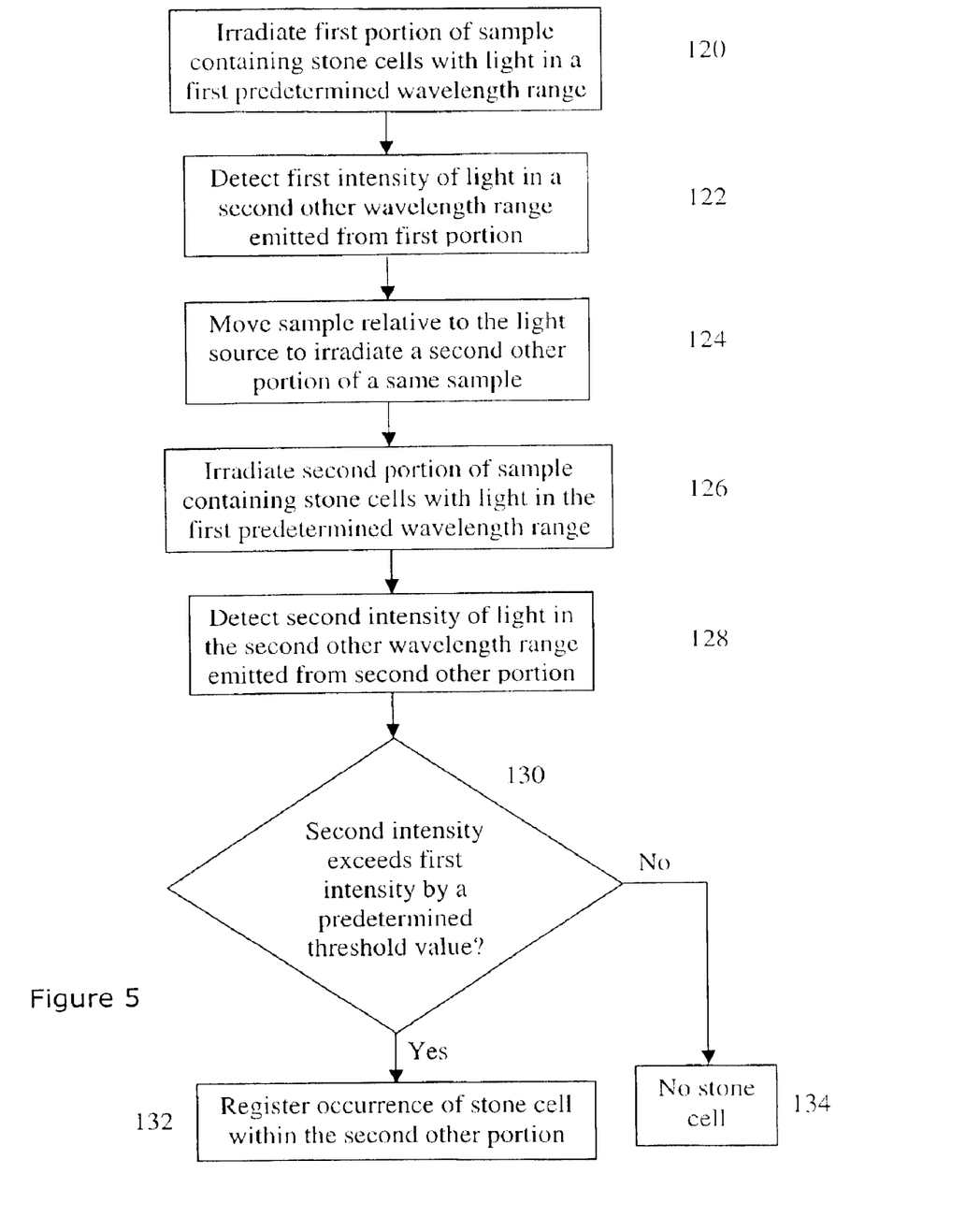
FIG. 5 is a simplified flow diagram of yet another method according to the instant invention.

Referring now to FIG. 5, shown is yet another method according to the instant invention. According to the method of FIG. 5, a first portion of the sample is irradiated with light in a predetermined wavelength range at step 120, the predetermined wavelength range being selected to induce the first portion of the sample to emit light in a second other wavelength range by fluorescence. An intensity of the light emitted in the second other wavelength range within the first portion is detected at step 122. At step 124, the sample is moved relative to the light source to irradiate at step 126 a second other portion of the sample with light in the predetermined wavelength range. At step 128, an intensity of the light emitted in the second other wavelength range within the second portion is detected. At decision step 130, it is determined whether or not the detected intensity of the light emitted within the second portion exceeds the detected intensity of the light emitted within the first portion by a predetermined threshold value. When yes, then at step 132 an occurrence of a stone cell within the second portion is registered. When no, then at step 134 no stone cell is registered. For instance, the intensity of light emitted by the stone cell is required to exceed the intensity of light emitted by the fiber matrix background by a predetermined amount in order for the occurrence of a stone cell to be registered. Otherwise, no stone cell is registered.

Figure 6:
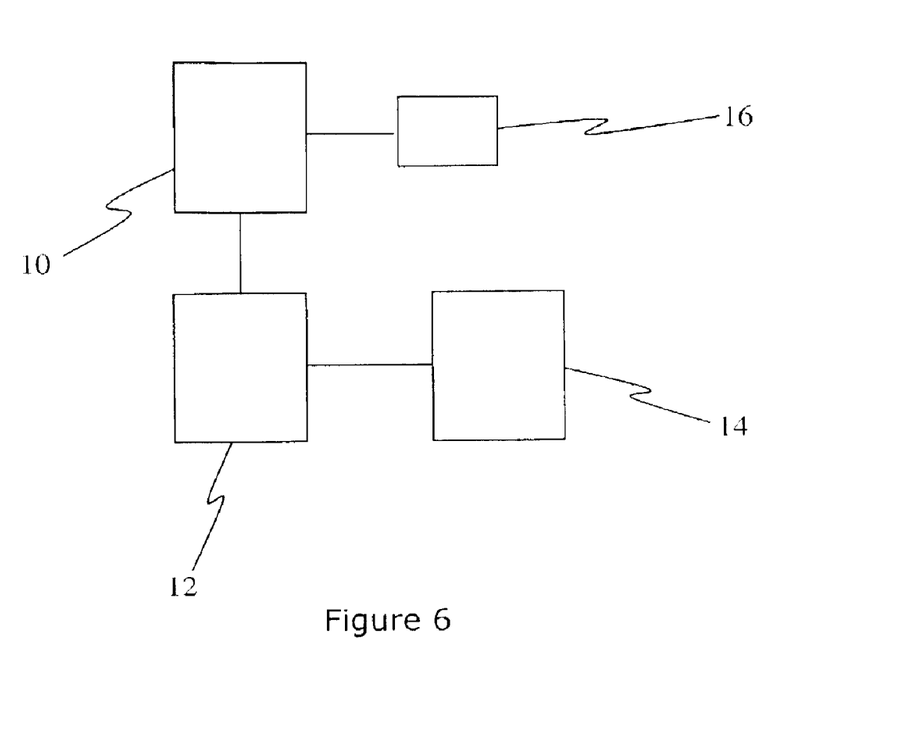
FIG. 6 is a schematic block diagram of a pulp and paper mill including an apparatus according to the instant invention for controlling an aspect of a pulp processing process.
Figure 7:
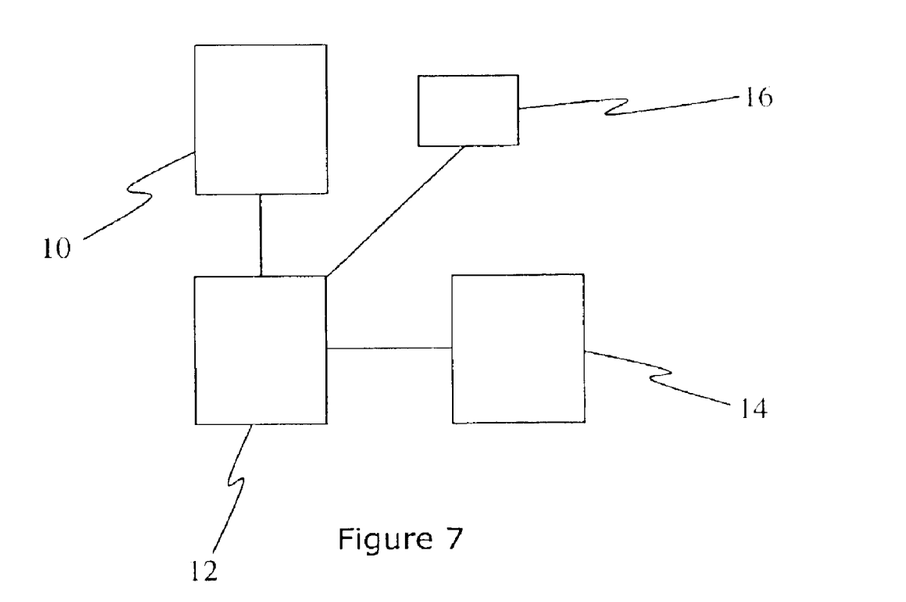
FIG. 7 is a schematic block diagram of a pulp and paper mill including an apparatus according to the instant invention for controlling an aspect of a paper making process.
Figure 8:
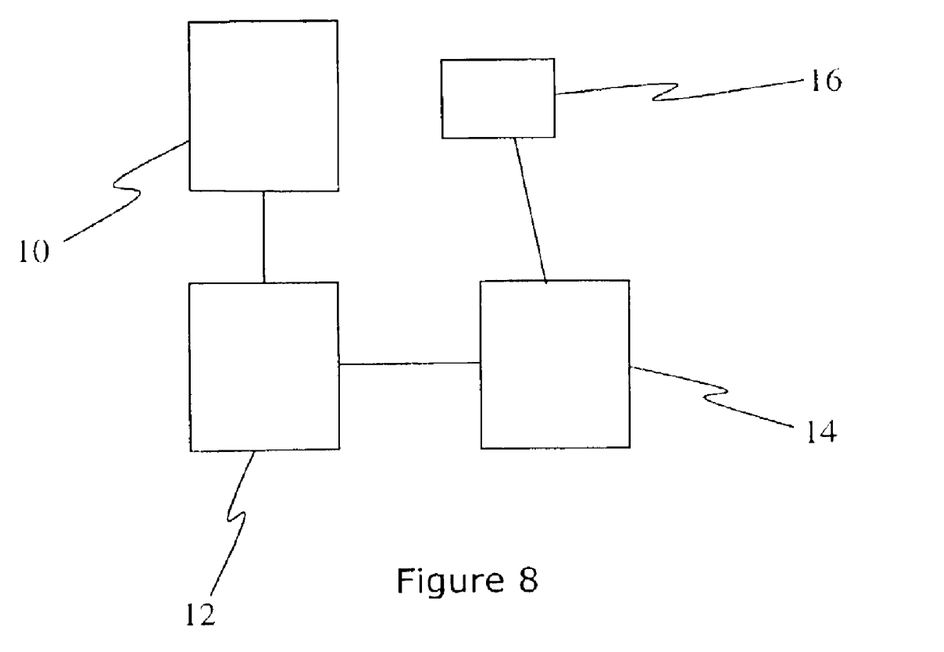
FIG. 8 is a schematic block diagram of a pulp and paper mill including an apparatus according to the instant invention for controlling an aspect of a paper finishing process.

Referring to FIGS. 6 to 8, shown are schematic block diagrams of a pulp and paper mill including an apparatus 16 according to the instant invention for controlling an aspect of a process. The apparatus is, for example, embodied as the apparatus of FIG. 1, the apparatus 16 being adapted to operate in a substantially automated manner. The pulp and paper mill includes a pulp-slurry processing portion 10, a papermaking portion 12, and a paper-finishing portion 14. For instance, pulp-processing steps such as bleaching and/or delignification are performed at the pulp-slurry processing portion 10 to produce a pulp-slurry having predetermined characteristics. The processed pulp is fed to a conveyor-type belt and water contained therein is expelled prior to forming of sheets or rolls of paper at the papermaking portion 12. Additionally, the paper sheets or rolls are provided to the paper-finishing portion 14 to be cut to size, etc. Optionally, one or more portions are absent from the mill. Further optionally, the mill includes additional portions.

Referring now to FIG. 6, shown is a schematic block diagram of a pulp and paper mill including an apparatus according to the instant invention for controlling an aspect of a pulp processing process. The apparatus 16 is in communication with the pulp-slurry processing portion 10 for receiving a pulp slurry sample therefrom. For instance, the apparatus 16 is an on-line analyzer for automatically sampling and analyzing the pulp slurry from the pulp-slurry processing portion 10. The apparatus 16 further includes a feedback control circuit (not shown) for adjusting a parameter of the pulp-slurry processing portion 10 to achieve a desired result in dependence upon an analysis of the pulp slurry. For instance, the feedback control circuit is for one of: adding a feed component to the pulp-slurry; adjusting a temperature of the pulp-slurry; adjusting a mixing rate of the pulp-slurry, etc. Optionally, another parameter affecting the pulp-slurry is adjusted. Further optionally, the apparatus 16 is adapted to automatically sample one of the pulp slurry and a fluid extracted from the pulp slurry.

Figure 9:
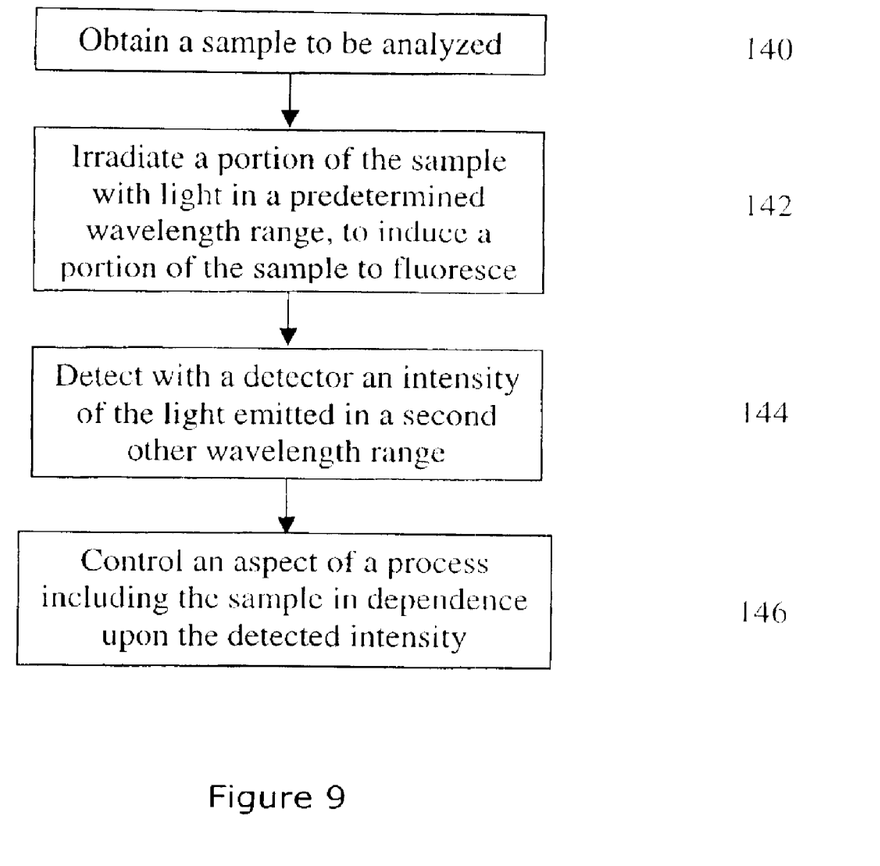
FIG. 9 is a simplified flow diagram of a method for controlling automatically an aspect of a pulp and paper making process; and, FIG. 10 shows a gray value histogram from a Confocal Microscope Image.

Referring now to FIG. 9, shown is a simplified block diagram of a method for controlling automatically an aspect of a pulp and paper making process. The description of FIG. 9 is presented hereinafter by way of a specific and non-limiting example in which the process is a pulp processing process for producing a pulp-slurry having a predetermined characteristic. At step 140 a sample from the pulp-processing portion 10 is obtained for analysis. Preferably, the sample is obtained in an automated manner. The sample is prepared for analysis, and at step 142 a portion of the sample is irradiated with light in a predetermined wavelength range using the apparatus 16, to induce the portion of the sample to fluoresce. At step 144 the intensity of fluorescence is detected, for instance a detector of apparatus 16 is used to measure light emitted in a second other wavelength range from the portion of the sample. At step 146, an aspect of the pulp-slurry processing portion 10 is controlled in dependence upon the detected intensity. For example, the feedback control circuit of apparatus 16 carries a feedback control signal to a valve of the pulp-slurry processing portion 10 for adjusting a rate of addition of an input component to the pulp-slurry processing portion 10. Preferably, additional samples are obtained and analyzed at different times, such that the aspect of the process is adjusted repeatedly and by small increments, to achieve a desired result. For example, the desired result is a pulp product having a stone cell count that is within a predetermined range of values.

Referring now to FIG. 7, shown is a schematic block diagram of a pulp and paper mill including an apparatus according to the instant invention for controlling an aspect of a papermaking process. Elements labeled with the same numerals have the same function as those illustrated in FIG. 6. As shown in FIG. 7, the apparatus 16 is in communication with the papermaking portion 12 for receiving a sample therefrom. For example, the sample is in the form of one of a suspension of pulp in a process fluid, a pulp mat having some of the process fluid extracted by pressing and a portion of process fluid extracted from the pulp mat. Referring again to FIG. 9, the sample is prepared for analysis, and at step 142 a portion of the sample is irradiated with light in a predetermined wavelength range using the apparatus 16, to induce the portion of the sample to fluoresce. At step 144 the intensity of fluorescence is detected, for instance a detector of apparatus 16 is used to measure light emitted in a second other wavelength range from the portion of the sample. At step 146, an aspect of the papermaking portion 12 is controlled in dependence upon the detected intensity. For example, when the detected intensity is indicative of a stone cell count that is outside a predetermined range of values, the feedback control circuit of apparatus 16 carries a feedback control signal to a pulp-feeding member to adjust a pulp feed rate and the papermaking rate. Accordingly, when a high stone cell count is detected, the feed rate is decreased such that breakage of the forming sheet of paper does not occur. Of course, avoiding breakage of the forming sheet reduces downtime resulting in higher productivity. Optionally, the pulp feed is redirected for further processing before being formed into paper.

Referring now to FIG. 8, shown is a schematic block diagram of a pulp and paper mill including an apparatus according to the instant invention for controlling an aspect of a paper finishing process. Elements labeled with the same numerals have the same function as those illustrated in FIG.

6. During such postproduction processing, typically large sheets or rolls of paper are cut to size and packaged. According to the instant invention, an apparatus 16 is provided in communication with the paper-finishing portion 14. Referring again to FIG. 9, at step 140 a sample is obtained for analysis. The sample is, for instance, a portion of a sheet or roll of paper that is to be cut to size. At step 142 a portion of the sample is irradiated with light in a predetermined wavelength range using the apparatus 16, to induce the portion of the sample to fluoresce. At step 144 the intensity of fluorescence is detected, for instance a detector of apparatus 16 is used to measure light emitted in a second other wavelength range from the portion of the sample. At step 146, an aspect of the papermaking portion 12 is controlled in dependence upon the detected intensity. For example, when the detected intensity is indicative of a stone cell count that is outside a predetermined range of values, the feedback control circuit of apparatus 16 carries a feedback control signal to a cutting member to prevent cutting of the paper until a subsequent measurement is indicative of a stone cell count that is within the predetermined range of values. Optionally, the paper is cut to size prior to being analyzed, and sorted as to quality on the basis of the detected intensity.

Preliminary testing has shown a strong fluorescence signal for the stone cell and a small response from the surrounding fiber. The propensity of the stone cells to fluorescence was determined experimentally using a confocal microscope where the sample was excited at 488 nm and detected using a camera. The images were analyzed for their brightness levels, which are summarized in Table 1, below. When the average gray level is high it means the fluorescence intensity is great indicating a bright object or one that fluoresces. Low gray levels mean the picture is dark and fluorescence intensity is low.

TABLE 1

Average Gray Levels from Confocal Microscope Images.

|  | Paper and stone cell | Paper | Stone cells | Pulp |
|---|---|---|---|---|
| Average gray level | 106 | 75 | 106 | 19 |

Figure 10:
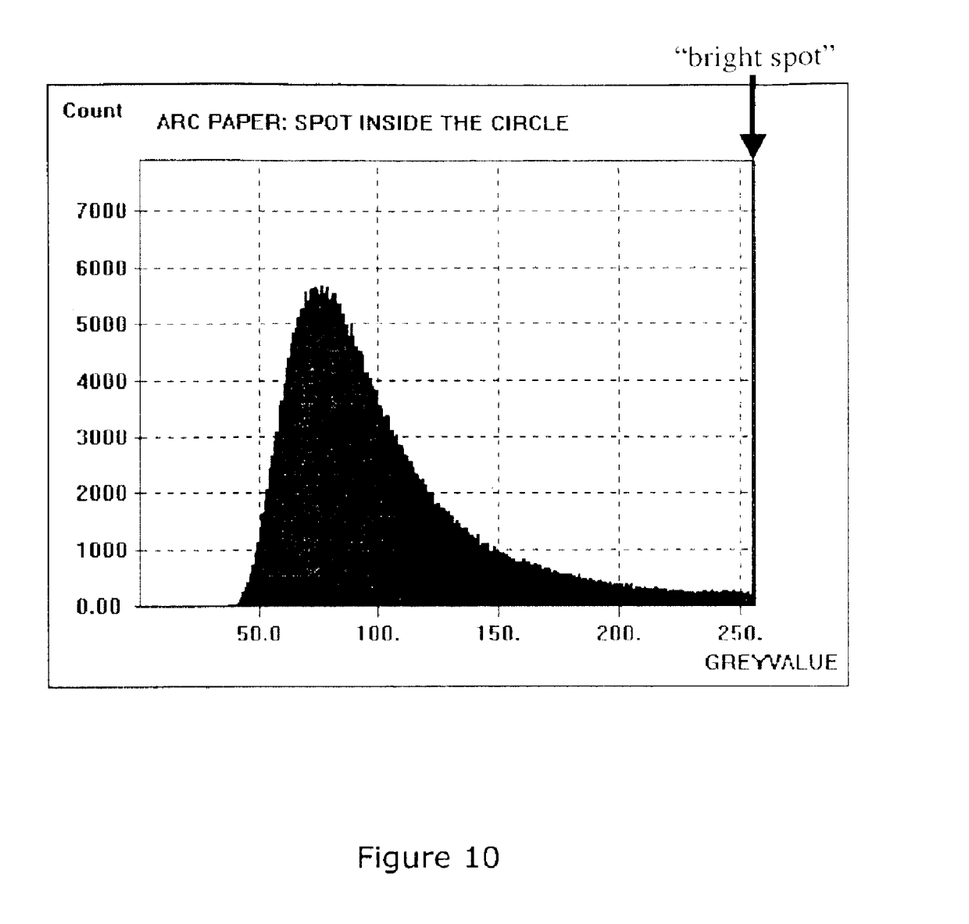

The paper or pulp and the stone cell have very different gray values making it easy to distinguish between them. Referring now to FIG. 10, the gray value histogram shows this to a greater extent where for this analysis each of the pixels in an image has a value of gray from black at 1 to white at 256. The number of pixels at each gray level is counted and the histogram is plotted. The large number of counts at 256 indicates an intense "bright spot", for example a stone cell fluorescing. The counts at lower gray levels are from the paper fiber matrix. The stone cell strongly fluoresces and will appear as a bright spot against the darker background that can be counted and quantified.

Numerous other embodiments may be envisaged without departing from the spirit and scope of the invention.

What is claimed is:

1. A method for detecting stone cells in a sample of wood pulp or paper comprising the steps of:
    a) irradiating a portion of the sample with light in a predetermined wavelength range, the predetermined wavelength range selected to induce some of the portion of the sample to emit light in a second other wavelength range by fluorescence;
    b) detecting with a detector an intensity of the light in the second other wavelength range emitted from some of the portion of the sample; and,
    c) registering a stone cell within the portion of the sample in dependence upon the detected intensity being within a predetermined range of intensity values.

2. A method according to claim 1 wherein the step of irradiating a portion of the sample with light in a predetermined wavelength range includes the steps of:
    providing an incident light source for launching incident light along an optical path including the portion of the sample; and
    filtering the incident light to selectively pass the light in the predetermined wavelength range to the portion of the sample, and to selectively block light in the second other wavelength range.

3. A method according to claim 1 including the step of filtering the light emitted from some of the portion of the sample, to selectively pass light in the second other wavelength range to the detector prior to detecting the intensity thereof.

4. A method according to claim 1 wherein the step of detecting the intensity of the light in the second other wavelength range includes a step of capturing an image of the portion of the sample being irradiated by the light in the predetermined wavelength range.

5. A method according to claim 4 wherein the image is captured absent magnification.

6. A method according to claim 4 wherein the image is a digital image comprising a plurality of individual pixels.

7. A method according to claim 1 wherein the wood pulp is provided as a thin smooth layer.

8. A method for determining a quality factor for a sample of wood pulp or paper comprising the steps of:
    a) providing a sample of wood pulp or paper;
    b) irradiating a portion of the sample with light in a predetermined wavelength range, the predetermined wavelength range selected to induce some of the portion of the sample to emit light in a second other wavelength range by fluorescence;
    c) detecting with a detector an intensity of the light emitted in the second other wavelength range from some of the portion of the sample; and
    d) determining the quality factor for the portion of the sample in dependence upon the detected intensity and a known threshold value.

9. A method according to claim 8 wherein the quality factor is indicative of a location of a stone cell within the portion.

10. A method according to claim 9 wherein the known threshold value is indicative of an emission of light in the second other wavelength range that is strong relative to an emission of light in the second other wavelength range from a non-stone cell portion of the sample.

11. A method according to claim 8 wherein the known threshold value is determined by a step of calibration.

12. A method according to claim 11 wherein the step of calibration comprises the step of adjusting a sensitivity of the detector such that an output value from the detector is indicative of the quality factor.

13. A method according to claim 8 wherein the step of irradiating a portion of the sample with light in a predetermined wavelength range includes the steps of:
    providing an incident light source for launching incident light along an optical path including the portion of the sample; and,
    filtering the incident light to selectively pass the light in the predetermined wavelength range to the portion of the sample, and to selectively block light in the second other wavelength range.

14. A method according to claim 8 including the step of filtering the light emitted from some of the portion of the sample, to selectively pass the light in the second other wavelength range to the detector prior to detecting the intensity thereof.

15. A method according to claim 8 wherein the step of detecting the intensity of the light emitted in the second other wavelength range includes the step of capturing an image of the portion of the sample being irradiated by the light in the predetermined wavelength range.

16. A method according to claim 15 wherein the image is captured absent magnification.

17. A method according to claim 15 wherein the image is a digital image comprising a plurality of individual pixels.

18. A method according to claim 8 wherein the step of detecting the intensity of the light includes a step of analyzing the emitted light in the second other wavelength range, to determine an area of high intensity of emitted light within the portion of the sample.

19. A method according to claim 8 wherein the wood pulp is provided as a thin smooth layer.

20. A method according to claim 8 including the steps of:
moving the sample relative to a source of the incident light to irradiate a second different portion of a same sample;
repeating steps a) to d) for the second different portion; and
comparing the determined quality factor for the portion and the determined quality factor for the second different portion, to identify a quality factor change that is indicative of a change in the quality of the wood pulp or paper sample.

21. A method according to claim 8 wherein the quality factor is indicative of a property of the wood pulp or paper sample selected from a group including: brightness of the sample; weight percent of residual lignin contained in the sample; and, delignification efficiency.

22. A method for detecting stone cells in a sample of wood pulp or paper comprising the steps of:
a) providing a light source for irradiating a first portion of the sample with light in a predetermined wavelength range, the predetermined wavelength range selected to induce some of the first portion of the sample to emit light in a second other wavelength range by fluorescence;
b) detecting an intensity of the light emitted in the second other wavelength range from some of the first portion;
c) moving the sample relative to the light source to irradiate a second other portion of the sample with light in the predetermined wavelength range;
d) detecting an intensity of the light emitted in the second other wavelength range from some of the second portion; and,
e) when the detected intensity of the light emitted from some of the second portion exceeds the detected intensity of the light emitted from some of the first portion by a predetermined threshold value, registering an occurrence of a stone cell within the second portion.

23. An apparatus comprising:
a holder for holding a sample of wood pulp or paper having therein stone cells;
a light source for irradiating a portion of the sample with light including light within a predetermined wavelength range, for inducing the portion of the sample to emit light in a second other wavelength range by fluorescence;
a detector for detecting an intensity of the light emitted in the second other wavelength range from the portion of the sample and for providing a signal in dependence thereof; and,
an analyzer for analyzing the signal provided by the detector to determine, in use, a quality factor for the portion of the sample in dependence upon the detected intensity.

24. An apparatus according to claim 23 including a first filter disposed between the light source and the holder for selectively transmitting the light within a predetermined wavelength range.

25. An apparatus according to claim 23 including a filter disposed between the holder and the detector, the filter for filtering the light within the predetermined wavelength range.

26. An apparatus according to claim 24 including a second filter disposed between the holder and the detector, the second filter for filtering the light within the predetermined wavelength range.

27. An apparatus according to claim 26 wherein the analyzer comprises a processor for analyzing automatically the signal provided by the detector.

28. An apparatus according to claim 26 wherein the detector comprises a camera for capturing an image of a predetermined area of the sample including the irradiated portion.

29. An apparatus according to claim 26 wherein the holder comprises a table moveable in a raster fashion.

30. An apparatus according to claim 26 wherein the light source is selected from a group comprising: a mercury vapor lamp; a deuterium lamp; a tungsten filament lamp; and, a laser.

31. An apparatus according to claim 26 wherein the holder includes a non-reflecting background for supporting a pulp sample applied thereto.

32. An apparatus according to claim 26 comprising a control circuit in communication with the analyzer for providing a control signal for use in controlling a paper manufacturing process.

33. An apparatus according to claim 26 comprising an output display in communication with the analyzer for providing an indication of a location of a stone cell.

34. An apparatus according to claim 26 comprising a computer readable medium having stored therein program code for in execution performing a step of determining the quality factor for the portion of the sample.

* * * * *